Figure 1:
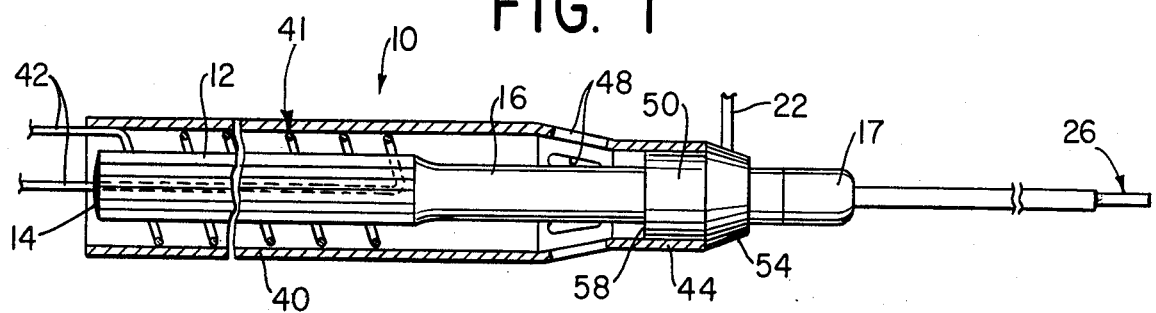

United States Patent [19]

Banko

[11] 4,406,284
[45] Sep. 27, 1983

[54] ULTRASONIC HANDPIECE DESIGN

[75] Inventor: Anton Banko, Bronx, N.Y.

[73] Assignee: Surgical Design Corp., Long Island, N.Y.

[21] Appl. No.: 245,667

[22] Filed: Mar. 20, 1981

[51] Int. Cl.³ .............................................. A61B 17/32
[52] U.S. Cl. .................................. 128/303 R; 433/86; 433/119; 310/26
[58] Field of Search .................... 128/303 R, 305, 276, 128/24 A, 320; 433/86, 119; 310/26

[56] References Cited

U.S. PATENT DOCUMENTS

| | | | |
|---|---|---|---|
| 2,128,562 | 12/1955 | Bailey | 433/119 X |
| 3,086,288 | 4/1963 | Balemuth et al. | 433/119 X |
| 3,335,443 | 8/1967 | Parisi et al. | 433/119 X |
| 3,427,480 | 2/1969 | Robinson | 310/26 X |
| 3,930,173 | 12/1975 | Banko | 310/26 |

FOREIGN PATENT DOCUMENTS 2418652  11/1979  France ................................. 433/119

Primary Examiner—Lee S. Cohen
Attorney, Agent, or Firm—Darby & Darby

[57] ABSTRACT

An ultrasonic instrument including a stack of laminations having acoustic impedance transformer connected and a housing which fits over the stack and at least a part of the transformer in which the housing has a portion of a material having a low coefficient of friction which makes contact with the acoustic impedance transformer.

8 Claims, 2 Drawing Figures

ULTRASONIC HANDPIECE DESIGN

Various types of ultrasonic handpieces are used in dental and medical applications. These include, for example, ultrasonic scalers which are used for dental purposes and ultrasonic surgical instruments such as, for example, used in microsurgery. Typical handpieces are shown in my U.S. Pat. Nos. 3,528,410, granted Sept. 15, 1970; 3,805,787, granted Apr. 23, 1974; and 3,930,173, granted Dec. 30, 1975, all of which are assigned to the same assignee.

In general, such handpieces are are formed of a stack of laminations to which is connected an acoustic impedance transformer. A work tip is connected to the acoustic impedance transformer. A housing is provided which fits around the laminations and a portion of the acoustic impedance transformer. The housing often has embedded therein the coils for providing the electrical energy to the laminations.

In general, the major direction of vibration of the acoustic impedance transformer is longitudinal of the length of the handpiece. When the housing is attached to the transducer, it is often desired to attach it at a nodal point of the acoustic impedance transformer thereby to reduce the amount of energy which is transmitted from the transformer to the housing and to reduce the heat generated. In general, it is not possible to totally eliminate the transfer of energy and there is always some amount of heat which is transmitted from the transformer to the housing due to the longitudinal vibration of the transformer. In the past, various arrangements such as O-rings have been utilized to attempt to reduce the amount of heat which is transmitted.

The present invention relates to an improved handpiece and, more particularly, to an improved housing for an ultrasonic handpiece. In accordance with the invention, the portion of the housing which is in contact with the acoustic impedance transformer is made of a material having a low coefficient of friction. The use of the low coefficient material reduces the coefficient of friction between the transformer and the housing as the transformer vibrates longitudinally.

It is therefore an object of the present invention to provide an improved ultrasonic handpiece.

A further object is to provide an improved ultrasonic handpiece in which the housing is connected to a handpiece acoustic impedance transformer by the use of a bushing having a low coefficient of friction.

An additional object is to provide an ultrasonic handpiece in which the housing is connected to the handpiece without the necessity of O-rings and in which the coupling has reduced friction.

Figure 2:
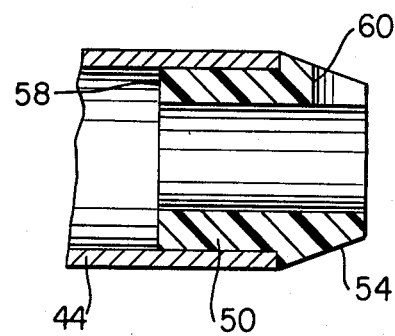

Other objects and advantages of the present invention will become more apparent upon reference to the following specification and annexed drawings in which:

FIG. 1 is a longitudinal view of the ultrasonic transducer portion of the handpiece; and FIG. 2 is a longitudinal view of the improved housing.

Referring to FIG. 1, the ultrasonic transducer 10 includes a stack of laminations 12 of a suitable material, for example, MONEL. The laminations are connected together at the non-working end 14 of the handpiece and are connected at the other end to one end of an acoustic impedance transformer 16. The acoustic impedance transformer is a body of metal of suitable shape and thickness necessary to convert the vibrations of the laminations 12 into longitudinal motion. The acoustic impedance transformer 16 has an end 17 to which a work tip 26 is connected. Tip 26 can be hollow or can be solid and surrounded by a shield. In either case there is provided a fluid flow passage to the end 17 of the acoustic impedance transformer. The passage can be used for infusion and/or evacuation fluid and material flow. There is a passage (not shown) through the transformer which communicates with the passage of the tip and a fitting 22 which extends external of the tube. Fitting 22 is used to connect to a source of evacuation pressure or inflow fluid. The particular flow arrangement is only illustrative since, for example, a solid tip can be used with a surrounding shield to form the passage, as in my aforesaid patent.

The transducer operates to produce longitudinal movement of the work tip 26. When the tip is immersed in a fluid or other medium, there will be a component of force produced which will be normal to the flat surface of the tip. This component of force will move a column of fluid to provide a force on the material being operated upon.

The handpiece has a sleeve or housing 40 which fits over the stack of laminations and at least a portion of the acoustic impedance transformer. The housing is preferably of a suitable plastic material. The portion of the housing 40 which fits over the stack has embedded therein or fastened thereto a coil of wires 41 from which leads 42 extend. The current is supplied to the coil 41 via the leads 42 so that the stack of laminations can be energized. The forward end 44 of the housing is tapered down fron the remainder and is provided at the transition area with a number of cooling slots 48.

An insert, or bushing, 50 of a low coefficient of friction material non-elastic, for example TEFLON, is provided. This material has a much lower coefficient of friction than the remainder of the housing. The insert 50 has a tapered head end 54 and a rearwardly extending neck 58 of reduced diameter which fits inside of the reduced diameter portion 44 of the housing. The insert 50 is sealed to the housing by any suitable adhesive.

The insert 50 is also provided with an opening, or slot, 60 to accommodate the outlet 22 for the infusion-/evacuation line of the tip of the handpiece.

When the housing is placed over the lamination stack and acoustic impedance transformer, the insert 50 provides a tight engaging fit with the acoustic impedance transformer. Since there is no fluid flow through the housing, no O-ring seals are necessary. The evacuation line fitting 22 fits within the slot 60 so that the housing is fully located on the transformer. The user can now hold the entire handpiece by the housing and he will not be in contact with any of the electrical components.

During the operation of the handpiece, current is supplied to the leads 42 to energize the coil 41 and the lamination stack. As the acoustic impedance transformer vibrates longitudinally, the friction between it and the insert 50 is reduced to a very small amount due to the use of the low coefficient friction material. Since the friction is reduced, the heat generated in the area of mounting the housing to the transducer is also reduced. The cooling slots 48 also serve to dissipate the heat. This is advantageous since the person holding the handpiece by the housing will encounter only a small or moderate amount of heat and he will not be subjected to discomfort.

What is claimed is:

1. An ultrasonic instrument comprising:

means for converting electrical energy into longitudinal vibratory motion, workpiece means having one end coupled to said converting means and receiving the longitudinal vibratory motion of said converting means so that said workpiece also vibrates longitudinally, said workpiece means having a free work producing end spaced from said coupled end, a housing within which said converting means is located and from which the free work producing end of said workpiece means extends, and support means of a low coefficient of friction non-elastic material engaging said housing and said workpiece means to permit vibratory longitudinal sliding motion of said workpiece means relative to said housing.

2. An ultrasonic instrument as in claim 1 wherein said support means of low coefficient of friction non-elastic material is of a lower coefficient of friction material than the remainder of the housing.

3. An ultrasonic instrument as in claim 1 wherein said support means of low coefficient of friction non-elastic material comprises a bushing which is attached to said housing, said workpiece means moving longitudinally relative to said support means in a sliding relationship.

4. An ultrasonic instrument as in claim 1 wherein said workpiece means further comprises acoustic impedance transformer means connected between said converting means and said work producing end of said workpiece means for coupling the longitudinal vibratory motion of said converting means to said work producing end, said support means engaging said transformer means.

5. An ultrasonic instrument as in claim 4 wherein said support means of low coefficient of friction material comprises a bushing which is attached to said housing, said workpiece means moving longitudinally relative to said support means in a sliding relationship.

6. An ultrasonic instrument as in either of claims 2, 3 or 5 wherein said support means is of TEFLON.

7. An ultrasonic instrument as in either of claims 3 or 5 wherein said housing is larger than said workpiece means and there is an interior space between them, and further comprising means communicating with said workpiece means at a point remote from the interior space defined between the housing and the converting means for supplying fluid to said workpiece means.

8. An ultrasonic instrument as in either of claims 1, 3, or 5 wherein cooling slots are provided in said housing in the area adjacent said support means.

* * * * *